(12) United States Patent
Powell et al.

(10) Patent No.: US 11,904,326 B2
(45) Date of Patent: Feb. 20, 2024

(54) SYSTEM FOR COLLECTING AND HARVESTING ALGAE FOR BIOFUEL CONVERSION

(71) Applicant: MANTA BIOFUEL, Owings Mills, MD (US)

(72) Inventors: Ryan Joseph Powell, Reisterstown, MD (US); John William Sturgis, IV, Baltimore, MD (US); Maximilian Davis Marshall, Baltimore, MD (US); Scott Joseph Witte, Towson, MD (US)

(73) Assignee: MANTA BIOFUEL, Owings Mills, MD (US)

( * ) Notice: Subject to any disclaimer, the term of this patent is extended or adjusted under 35 U.S.C. 154(b) by 267 days.

(21) Appl. No.: 17/048,385

(22) PCT Filed: Apr. 17, 2019

(86) PCT No.: PCT/US2019/027851
§ 371 (c)(1),
(2) Date: Oct. 16, 2020

(87) PCT Pub. No.: WO2019/204423
PCT Pub. Date: Oct. 24, 2019

(65) Prior Publication Data
US 2021/0170424 A1    Jun. 10, 2021

Related U.S. Application Data

(60) Provisional application No. 62/659,391, filed on Apr. 18, 2018.

(51) Int. Cl.
*B03C 1/01* (2006.01)
*B03C 1/033* (2006.01)
(Continued)

(52) U.S. Cl.
CPC .............. *B03C 1/01* (2013.01); *B03C 1/0332* (2013.01); *B03C 1/286* (2013.01); *C12N 1/02* (2013.01);
(Continued)

(58) Field of Classification Search
CPC ......... B03C 1/01; B03C 1/0332; B03C 1/286; B03C 2201/18; B03C 2201/26; C12N 1/02; C12N 1/12
(Continued)

(56) References Cited

U.S. PATENT DOCUMENTS 3,365,599 A * 1/1968 Brzezinski ............... B03C 1/14
335/304
3,431,200 A    3/1969 Davis et al.
(Continued)

FOREIGN PATENT DOCUMENTS

CA   2825752 A1 * 8/2012 ............... B03C 1/00
CN   201520695 U    7/2010
(Continued)

OTHER PUBLICATIONS

Translation of CN205740456U (Year: 2016).*
(Continued)

*Primary Examiner* — Ekandra S. Miller-Cruz
(74) *Attorney, Agent, or Firm* — Gianna Julian Arnold; Saul Ewing LLP (57) ABSTRACT

Systems and methods for harvesting algae is de-scribed herein. The system can include an algae pool containing at least one algae organism; a magnetic particle storage unit adapted or configured to introduce at least one magnetic particle into the algae pool, wherein the at least one magnetic particle binds to the at least one algae organism to form at least one algae conjugate; and an algae harvester, including: at least one magnetic disc adapted or configured to
(Continued)

attach, via a surface of the at least one magnetic disc, to the at least one algae conjugate when the at least one algae conjugate comes in contact with the at least one magnetic disc; and at least one scraper adapted or configured to: remove the at least one algae conjugate from the surface of the at least one magnetic disc; and transport the at least one algae conjugate from the algae harvester.

29 Claims, 11 Drawing Sheets (51) Int. Cl.
B03C 1/28 (2006.01)
C12N 1/02 (2006.01)
C12N 1/12 (2006.01)

(52) U.S. Cl.
CPC ............ C12N 1/12 (2013.01); B03C 2201/18 (2013.01); B03C 2201/26 (2013.01)

(58) Field of Classification Search
USPC ........................................................ 210/695
See application file for complete search history.

(56) References Cited

U.S. PATENT DOCUMENTS

| | | | |
|---|---|---|---|
| 3,780,471 A * | 12/1973 | Ort | C02F 3/32 47/1.4 |
| 5,795,471 A * | 8/1998 | Naito | C02F 1/285 210/283 |
| 5,944,986 A | 8/1999 | Saho et al. | |
| 2014/0242663 A1 | 8/2014 | Nath et al. | |
| 2016/0310962 A1 * | 10/2016 | Suderman | B03C 1/247 |

FOREIGN PATENT DOCUMENTS

| | | | | |
|---|---|---|---|---|
| CN | 202688064 U | | 1/2013 | |
| CN | 205740456 U * | | 2/2016 | ................ C02F 1/48 |
| EP | 2659983 A2 * | | 5/2013 | ............. B03C 1/033 |
| WO | WO-1994011075 A1 * | | 5/1994 | ............. B01B 35/06 |
| WO | 2017019695 A1 | | 2/2017 | |

OTHER PUBLICATIONS

Translation of EP2659983A2 (Year: 2013).*
Translation of CN201520695U (cited in IDS) (Year: 2010).*
Translation of CN202688064U (cited in IDS) (Year: 2013).*

* cited by examiner

| Channel Size | Flow rate (L/min) | % Particle recovery under continuous operation | | | | |
|---|---|---|---|---|---|---|
| | | 1 min | 2 min | 3 min | 4 min | 5 min |
| 3/4" | 3 | 99.86 | 99.71 | 100.00 | 100.00 | 100.00 |
| 3/4" | 5 | 99.29 | 99.14 | 98.43 | 98.29 | 97.86 |
| 1" | 5 | 99.43 | 99.57 | 99.57 | 99.57 | 99.43 |
| 1" | 5 | 99.57 | 99.57 | 99.57 | 99.43 | 99.29 |
| 1" | 8 | 99.14 | 99.00 | 98.72 | 98.29 | 98.72 |
| 1" | 10 | 99.43 | 99.00 | 96.86 | 95.44 | 94.29 |

SYSTEM FOR COLLECTING AND HARVESTING ALGAE FOR BIOFUEL CONVERSION

CROSS REFERENCE TO RELATED APPLICATIONS

This application claims priority and benefit of PCT/US2019/027851, filed Apr. 17, 2019, which claims priority to U.S. Provisional Patent Application No. 62/659,391, filed Apr. 18, 2018, the entire contents of each of which are hereby incorporated in total by reference.

BACKGROUND OF THE INVENTION

Algal-derived biofuels are one of the best alternatives for economically replacing liquid fossil fuels with a fungible renewable energy source. Algae can accumulate more than 50% of their biomass in oil and can be grown in saline water on land not suitable for agriculture. These characteristics mean algal biofuels do not compete for fresh water and arable land with conventional food crops. In addition, less land will be needed to produce the needed fuel than is required for other biofuel feed stocks.

One major problem with algal biofuels is that the algae most suited for biofuel production are small in size and difficult to harvest. Efficient harvest is crucial because algae cultures yield at best a few grams of algae per liter of water. The algae must be separated from the water before they can be converted to fuel. At the laboratory scale, algae cultures can be harvested by centrifugation or filtration, but these methods are too energy- and capital-intensive for harvesting algae from the immense volumes of water needed for commercial scale production of algal biofuels. Chemical flocculation can be used at large scales, but requires treatment of the water after the algae are removed so the water can safely be reused or released into the environment.

Furthermore, nuisance algal blooms are a problem for private individuals, businesses and local governments alike. While algal blooms are unsightly for businesses, such as golf courses and housing developments, they pose a real health hazard when toxic algae are present. In the summer of 2014 about 500,000 residents in the city of Toledo, Ohio were cut off from their water supply due to a toxic algae bloom in Lake Erie. Residents could not drink or even bathe in public water due to the presence of toxins. During this crisis, the city of Toledo had no means of getting rid of the algae. The National Oceanic and Atmospheric Administration estimates that $82 million is lost in revenue per year for the United States due to harmful algal blooms. As another example, the city of Cleveland, Ohio spends $2 million per year when an algal bloom is present in Lake Erie.

There is a need for improved methods for collecting and harvesting algae for biofuel conversion.

SUMMARY OF THE INVENTION

It is an object of the invention to provide a system including: an algae pool containing at least one algae organism; a magnetic particle storage unit adapted or configured to introduce at least one magnetic particle into the algae pool, wherein the at least one magnetic particle binds to the at least one algae organism to form at least one algae conjugate; and an algae harvester, including: at least one magnetic disc adapted or configured to attach, via a surface of the at least one magnetic disc, to the at least one algae conjugate when the at least one algae conjugate comes in contact with the at least one magnetic disc; and at least one scraper adapted or configured to: remove the at least one algae conjugate from the surface of the at least one magnetic disc; and transport the at least one algae conjugate from the algae harvester. This object of the invention can have a variety of embodiments. The system can further include a conjugate separator adapted or configured to: receive the at least one algae conjugate from the algae harvester; and separate the at least one algae conjugate into the at least one magnetic particle and the at least one algae organism. Separating the at least one algae conjugate can further include reducing a calcium concentration of a solution containing the at least one algae conjugate.

The system can further include a hydrodynamic shear, where separating the at least one algae conjugate can further include shearing, via the hydrodynamic shear, the at least one algae conjugate. Separating the at least algae conjugate can further include magnetically separating the at least one algae conjugate. The at least one magnetic particle can be transported back to the algae pool after being separated from the at least one algae organism.

The at least one magnetic disc can be further adapted or configured to rotate along a center axis of the at least one magnetic disc. The scraper can be further adapted or configured to remove the at least one algae conjugate from the surface of the at least one magnetic disc as the at least one magnetic disc rotates along the center axis. Transporting the at least one algae conjugate can further include transporting the at least one algae conjugate back to the algae pool.

The at least one magnetic disc can further include a plurality of magnetic tiles. In varying embodiments, each magnetic tile includes a north magnetic pole and a south magnetic pole, or the plurality of magnetic tiles further comprise a plurality of north magnetic poles and a plurality of south magnetic poles, or the plurality of magnetic tiles further comprise at least one Holbach array, or there is a combination thereof. The plurality of magnetic tiles can be configured to form an aggregate north pole and an aggregate south pole for the at least one magnetic disc. The plurality of magnetic tiles can be configured to form a closed magnetic circuit within the at least one magnetic disc.

The plurality of magnetic tiles can form a plurality of magnetic field lines, where the plurality of magnetic field lines are configured in a parallel line pattern or a grid pattern. In some cases, a spacing between each south magnetic pole or north magnetic pole, and an adjacent magnetic pole is between 0.06 inches and 4 inches.

The algae harvester can be located within or on a surface of the algae pool. The system can further include an axial flow pump configured or adapted to transport the at least one algae organism from the algae pool to the algae harvester.

Another object of the invention is to provide a method for harvesting algae, the method including: introducing at least one magnetic particle into an algae pool containing at least one algae organism; binding the at least one magnetic particle to the at least one algae organism to form at least one algae conjugate; attaching, via a surface of at least one magnetic disc of an algae harvester, to the at least one algae conjugate when the at least one algae conjugate comes in contact with the at least one magnetic disc; removing, via a scraper, the at least one algae conjugate from the surface of the at least one magnetic disc; and transporting the at least one algae conjugate from the algae harvester.

This object of the invention can have a variety of embodiments. The method can further include receiving, by a conjugate separator, the at least one algae conjugate from the algae harvester; and separating the at least one algae conjugate into the at least one magnetic particle and the at least one algae organism. Separating the at least one algae conjugate can further include reducing a calcium concentration of a solution containing the at least one algae conjugate.

Separating the at least one algae conjugate can further include shearing, via a hydrodynamic shear, the at least one algae conjugate. Separating the at least algae conjugate can further include magnetically separating the at least one algae conjugate. The at least one magnetic particle can be transported back to the algae pool after being separated from the at least one algae organism.

The method can further include rotating the at least one magnetic disc along a center axis of the at least one magnetic disc. The method can further include removing, via the scraper, the at least one algae conjugate from the surface of the at least one magnetic disc as the at least one magnetic disc rotates along the center axis. Transporting: the at least one algae conjugate can further include transporting the at least one algae conjugate back to the algae pool.

The at least one magnetic disc further can further include a plurality of magnetic tiles, where each magnetic tile includes a north magnetic pole and a south magnetic polo, or a plurality of north magnetic poles and a plurality of south magnetic poles, at least one Holbach array, or a combination thereof. The plurality of magnetic tiles can be configured to form an aggregate north pole and an aggregate south pole for the at least one magnetic disc. The plurality of magnetic tiles can be configured to form a closed magnetic circuit within the at least one magnetic disc.

The plurality of magnetic tiles can form a plurality of magnetic field lines, where the plurality of magnetic field lines are configured in a parallel line pattern or a grid pattern. In some cases, a spacing between each south magnetic pole or north magnetic pole, and an adjacent magnetic pole is between 0.06 inches and 4 inches.

The algae harvester can be located within or on a surface of the algae pool. The method can further include transporting, via an axial flow pump, the at least one algae organism from the algae pool to the algae harvester.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

A system for collecting and harvesting algae for biofuel conversion and associated methods are described herein. In some embodiments, the system includes a harvester for harvesting algae from an algae source. The algae are bound to magnetic particles that are introduced to the algae source. The particle/algae combination is pumped through a series of magnetic discs in the harvester. The magnetic discs attract the particle/algae combination through magnetic attraction, where the particle/algae combination "attach" to the surface of one of the magnetic discs. Furthermore, the magnetic discs rotate about an axis, where the surface of the magnetic disc is in contact with a scraper. The scraper serapes the surface of the magnetic disc, thereby removing the particle/algae combination from the magnetic disc. The particle/algae combination is then funneled to a collection point, where the combination is then transported to a separator.

The system described herein thus allows for a cost-efficient technique for generating biofuel. The magnetic particle collection reduces the strength of water pumps utilized for transporting algae throughout the system. Further, the system is not limited to the collection and harvesting of certain types of algae and can therefore be used in a variety of settings, including toxic algae removal.

Figure 1:
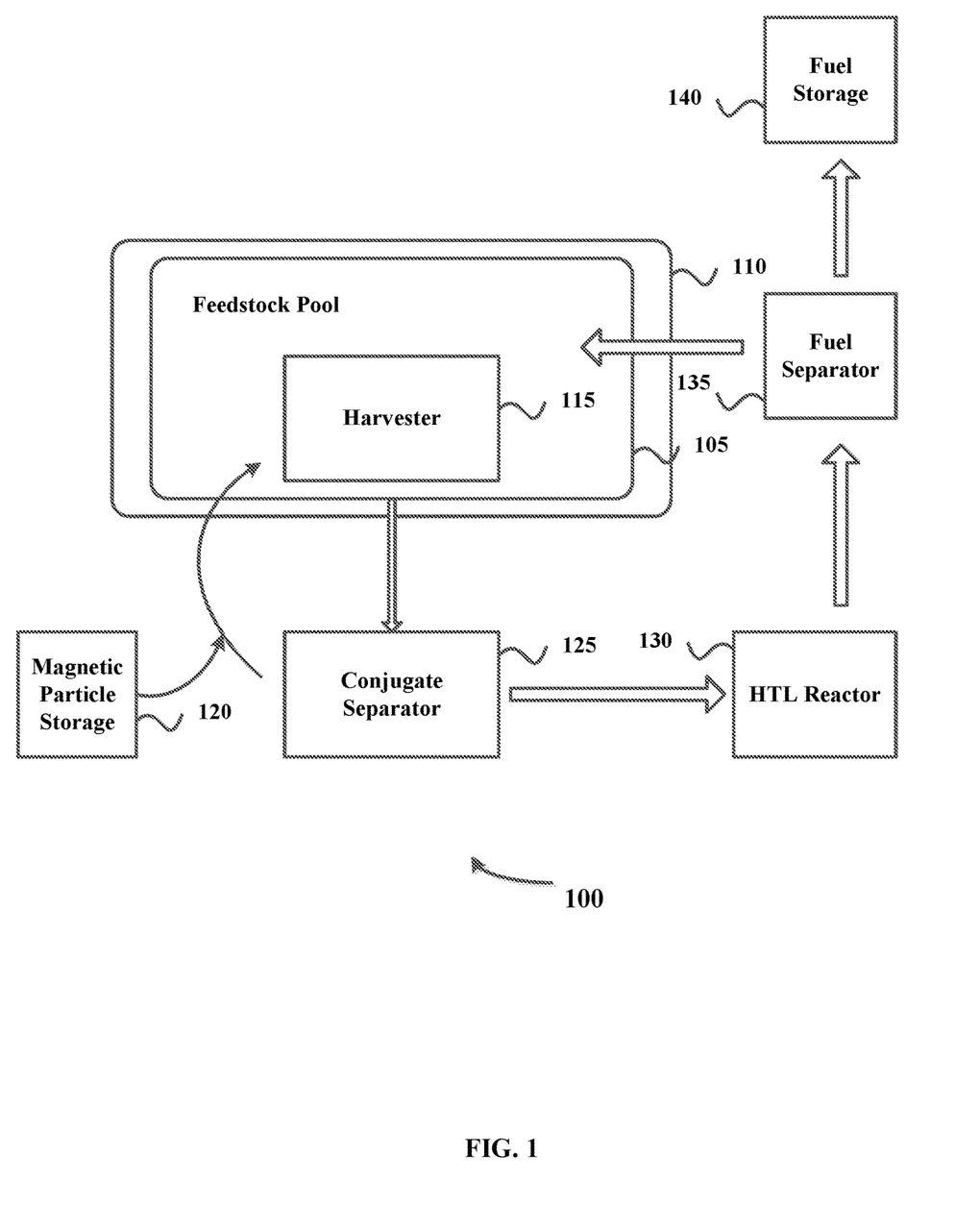
FIG. 1 depicts a system for harvesting and converting algae into biofuel, in accordance with embodiments of the claimed invention.

FIG. 1 depicts a system 100 for collecting and harvesting algae for biofuel conversion, according to the claimed invention. The system 100 includes a feedstock pool 105.

The feedstock pool 105 can contain a strain of algae, or in some cases multiple strains of algae.

The feedstock pool 105 is housed by an algal pond 110. The algal pond can, in some cases, be an unlined, above-ground structure. Additionally or alternatively, the algal pond 110 can be composed of earthen clay, which retains the feedstock pool 110. Eliminating the lining requirement allows for a significant reduction in algal pond 110 construction costs.

In certain embodiments, algae can be grown by adding manure to the algal pond 110. The nutrients in the manure stimulates the growth of a consortia of native algae species. Algal strains contemplated for collecting, harvesting or concentration herein can include, but are not limited to, *Phaeodactulum tricornutum, Chloreclla protothecoides, Nannochloropsis salina, Nannochloropsis sp. Tetraselmis succica, Tetraselmis chuii, Botrycoccus braunii, Chlorella sp., Chlorella ellipsoidea, Chlorella emersonii, Chlorella minutissima, Chlorella salina, Chlorella protothecoides, Chlorella pyrenoidosa, Chlorella sorokiniana, Chlorella vulgaris, Chroomonas salina, Cyclotella cryptica, Cyclotella sp., Dunaliella salina, Dunaliella hardawil, Dunaliella tertiolecta, Euglena gracilis, Gymnodinium nelsoni, Haematococcus pluvialis, Isochrysis galbana, Monoraphidium minutum, Monoraphidium sp., Neochloris oleoabundans, Nitzschia laevis, Onoraphidium sp., Pavlova lutheri, Phaeodactylum tricotnutum, Porphyridium cruentum, Scenedesmus obliquuus, Scenedesmus quadricaula Scenedesmus sp., Stichococcus bacillaris, Spirulina platensis, Thalassiosirs sp.* or combinations thereof.

The algae are harvested with magnetic particles. Magnetic harvesting particles are introduced to the feedstock pool 105 through a continuous harvester 115. In some cases, the magnetic particles can be stored in a magnetic panicle storage unit 120, which then introduces the magnetic particles into the harvester 115. For example, in one embodiment the magnetic particles are injected from a concentrated feed into the flow to obtain a final concentration of 1 g/L. In other embodiments the concentration of the particles can vary between 0.25 g/L-15 g/L. Binding of the algae to the magnetic particles is rapid (e.g., occurs in less than half a second). The magnetic panicles bind to the algae inside the harvester 115, and the particle-algae conjugates are removed from the algal pond 110 magnetically. Binding of the algae to the panicles is due to electrostatic attraction. The magnetic particles are positively charged and algae are negatively charged. These oppositely charged particles bind to form particle-algae conjugates.

The concentrated conjugates are transferred to a conjugate separator 125 where the magnetic particles are separated from the algae. In some cases the conjugate separator is external to the feedstock pool 105 (e.g., on shore). In some embodiments, the separated magnetic particles are reintroduced into the feedstock pool 105 to lower operating costs.

Figure 2:
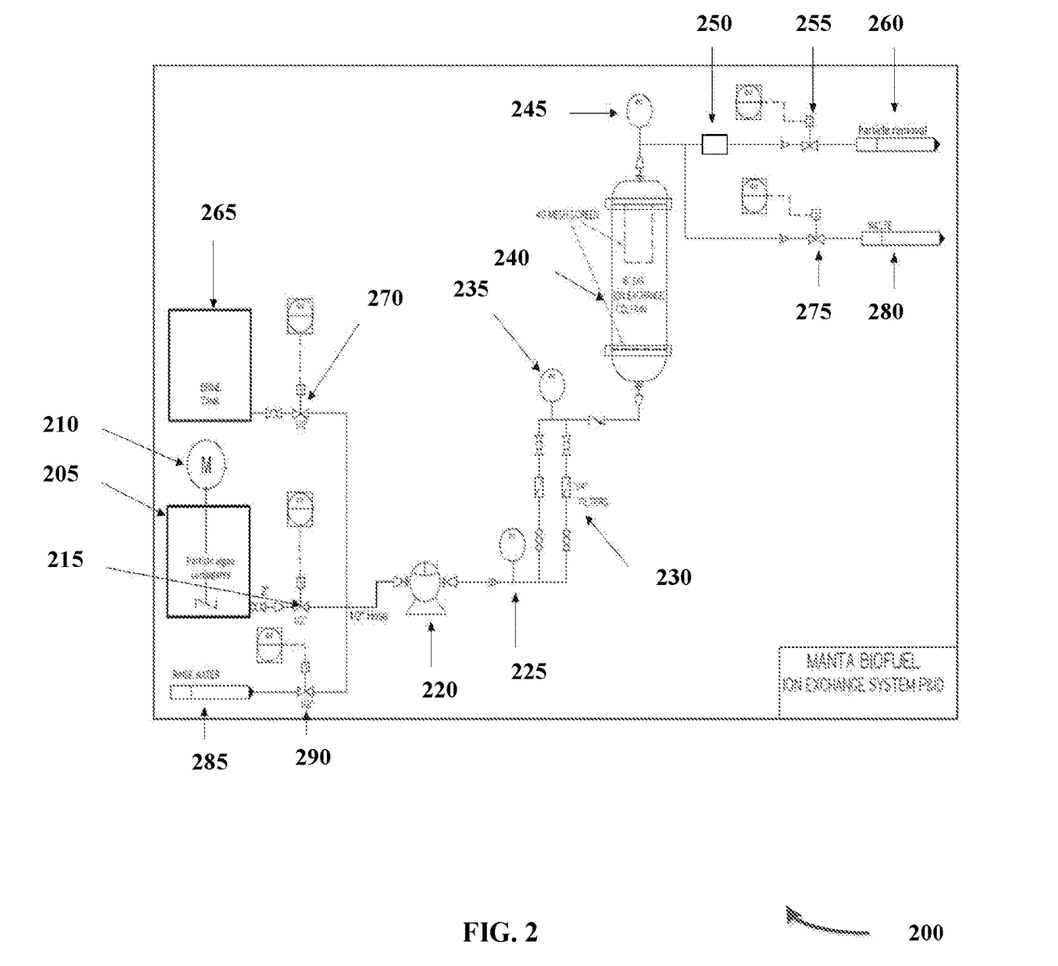
FIG. 2 depicts a system for separating algae/magnetic particle conjugates, in accordance with embodiments of the claimed invention.

Algae separation is achieved through a three-step process. First calcium concentration in the particle-algae conjugate solution is reduced. Next, a hydrodynamic shear is applied to the solution to physically separate the algae from the particles. Finally, the particles are separated from the algae with a magnetic separator. An example embodiment of this separation system is shown in FIG. 2. In this embodiment the particle-algae conjugates are stored in a tank 205 which is stirred by a motor 210. Control of the flow to a pump 220 is mediated by a control valve 215. Pressure of the flow immediately subsequent to the pump is monitored by a pressure gauge 225 before the flow passes through filters 230. Pressure of the flow after the filters is monitored by a pressure gauge 235. The difference between pressure gauges 225 and 235 allows for a determination of whether a filter begins to clog.

The flow then passes into a column 240 which is filled with cation exchange resin. Upon exiting the column, pressure of the flow is measured by a pressure gauge 245 before passing though the shearing apparatus 250. The shearing apparatus 250 can be but is not limited to a small-diameter orifice, an inline mixing fixture, or a vibrating fixture. Flow to the magnetic particle separator 260 is controlled by a control valve 255, inside the magnetic separator 260 the particles are magnetically removed from the flow, yielding a constant stream of concentrated algae. The magnetic particle separator 260 can be of various designs with either ferrite magnets, rare earth magnets or other similar magnets.

The resin in the column 240 is continuously depleted as it removes calcium from the particle-algae conjugates. As the resin becomes depleted the column 240 removes loss and less calcium from the flow. To regenerate the column 240, the flow control valve 215 is closed and a flow control valve 270 is opened to allow sodium chloride brine from a brine tank 265 to be introduced into the column 240. The control valve 255 is also closed and a control valve 275 is opened so the flow goes to waste 280. Brine is pumped by the pump 220 through the column 240 to regenerate the column 240. Next, the control valve 270 is closed and a control valve 290 is opened to allow rinse water 285 to be pumped through the column 240. After this cycle is completed the system can continue processing particle algae conjugates by closing control valves 275 and 290 and opening control valves 215 and 255.

Figure 3:
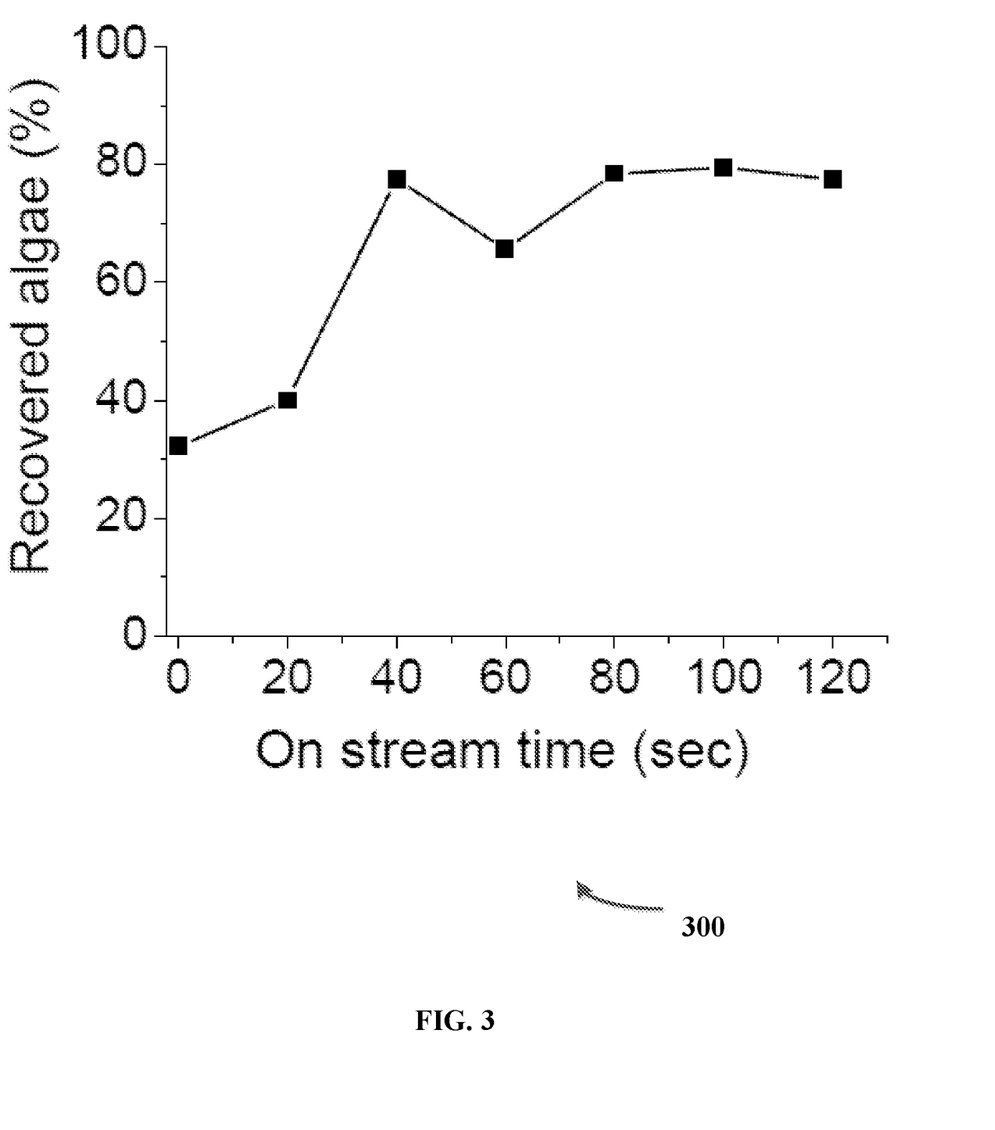
FIG. 3 depicts a graph of algae recovery rates for a separator, in accordance with embodiments of the claimed invention.

The lifetime of the resin has been tested with over 1,000 bed volumes and showed no signs of fouling. Testing data 300 are shown in FIG. 3. These data 300 depict the percent of algae recovered from the particles after the system is operational. The data 300 demonstrate that the system quickly stabilizes to a recovery rate of about 80%.

Figure 4:
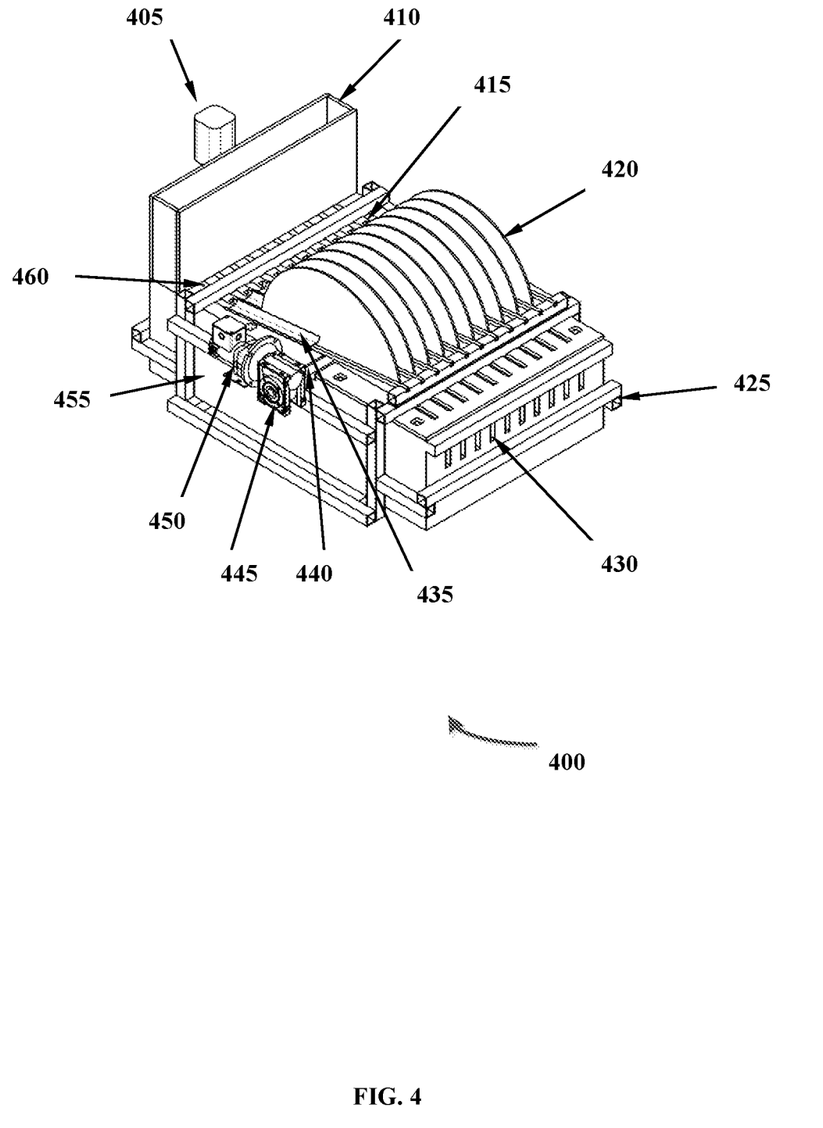
FIGS. 4 and 5 depict a magnetic algae harvester, in accordance with embodiments of the claimed invention.

FIG. 4 depicts an algae harvester 400 in accordance with embodiments of the claimed invention. In some cases, algae harvester 400 can be an example of harvester 115 as described with reference to FIG. 1.

Algae water is pumped from the environment, such as algal pond 110 of FIG. 1, by pump 405.

Magnetic particles are injected into the flow and bind to the algae, forming particle-algae conjugates. The particle-algae conjugates are then introduced into the algae harvester via plenum 410 into separation channels 460. The conjugates flow into the plenum 410 that separates the flow so that the conjugates are introduced evenly across the inflow of the separation chambers 460. The separation chambers 460 are contained within a shell 455 that is supported by a frame 425. Even introduction of the conjugate feedstock fluid ensures that each magnetic separator 420 receives the same flow rate.

The particle-algae conjugates flow past magnetic separators 420 that remove the conjugates from the water magnetically.

Conjugate separation is achieved using magnetic discs (e.g., separator 420). These discs are composed of one or more magnets. In some embodiments, each separator 420 can be composed of multiple magnets. In some of these embodiments, the magnets can be glued together with flexible epoxy. In some cases, magnets that are used to form a separator 420 include, but are not limited to, ferrite grades C1-C8 and their international equivalents.

The magnetic separators 420 can include different magnetic pole orientations. In one embodiment, each separator disc includes a dipole orientation where each disc separator 420 has a single north pole and south pole. Other embodiments include multipole arrays where each separation disc includes arrays of multiple north poles and south poles on each side of the disc. These fields can be arranged in either parallel lines or in a grid pattern with a spacing between each pole (e.g., between 0.06"-4"). In another embodiment, the discs include Halbach arrays. These arrays are similar to multipole magnets in that each face of the separator 420 has multiple poles. However, in a Halbach array, the magnetic field generate an internal circuit within the magnetic material. Thus, instead of the magnetic field traveling straight through two parallel surfaces of the magnet, the magnetic field completes a circuit in a parabola traveling from one adjacent pole to the other.

The now concentrated conjugates are removed from the magnetic separators 420 by rotating past fixed scrapers 435, The separators 420 are rotated via a driveshaft 440. The driveshaft 440 is turned by an electric motor 450 through a turndown gearbox 445. As the separators 420 are rotated, a surface of a separator 420 comes into contact with, or in close proximity to, a surface of a scraper 435. If a conjugate is present on the surface of the separator 420 as the separator is rotated, the conjugate is scraped from the surface of the separator 420. In some cases, the conjugate is transferred over to the surface of the scraper 435, additionally or alternatively, the conjugate can be transported to a funnel for further collection.

Scrapers 435 can be composed of flexible plastic. Additionally or alternatively, the scraper 435 can be compressed into a "U" shape between two adjacent magnetic separators 420. In one embodiment, the scraper 435 is a flexible piece of thin plastic (e.g., 0.016"-0.125" thick). In some cases, the scraper material is composed of ultra-high molecular weight polyethylene. However, other thermoset and thermoplastic materials can also be used.

The magnetic particles are scraped from the separation magnets either continuously or intermittently. If scraping occurs intermittently, the scrapers 435 can be operated at predetermined time periods. For example, in some embodiments scraping occurs between 10-600 seconds. In some cases, the collected conjugates can have a concentration of between 10-400 g/L depending on scraping frequency, feed concentration, and length of the scraping time.

The conjugates from multiple separators 420 are collected at a common point 415 in the harvester 400. The conjugates are then either be processed to remove the algae from the magnetic particles or reinjected back into the algal source (e.g., algal pond 110) to harvest more algae.

The collected conjugates are either moved on for processing and recovery of the algae from the particles or are reinjected into the system (e.g., reintroduced to the algal source). Reinjection increases mass loading onto the particles. If the particles are reinjected, the particles are introduced into a flow of fresh feedstock (e.g., fresh flow through the harvester). In some cases, this process can be continually be repeated for a predetermined number of cycles. Increasing particle cycling improves algal loading on the particles, but also successively reduces algae harvesting rates. In some embodiments, 3-5 cycles are optimal. Alternatively, in some embodiments as many as 15 cycles are used.

If the conjugates are moved on for processing, the algae may be separated from the magnetic particles (e.g., in conjugate separator 125 of FIG. 1) and transferred over to a HTL reactor, such as HTL reactor 130 as described with reference to FIG. 1.

Figure 5:
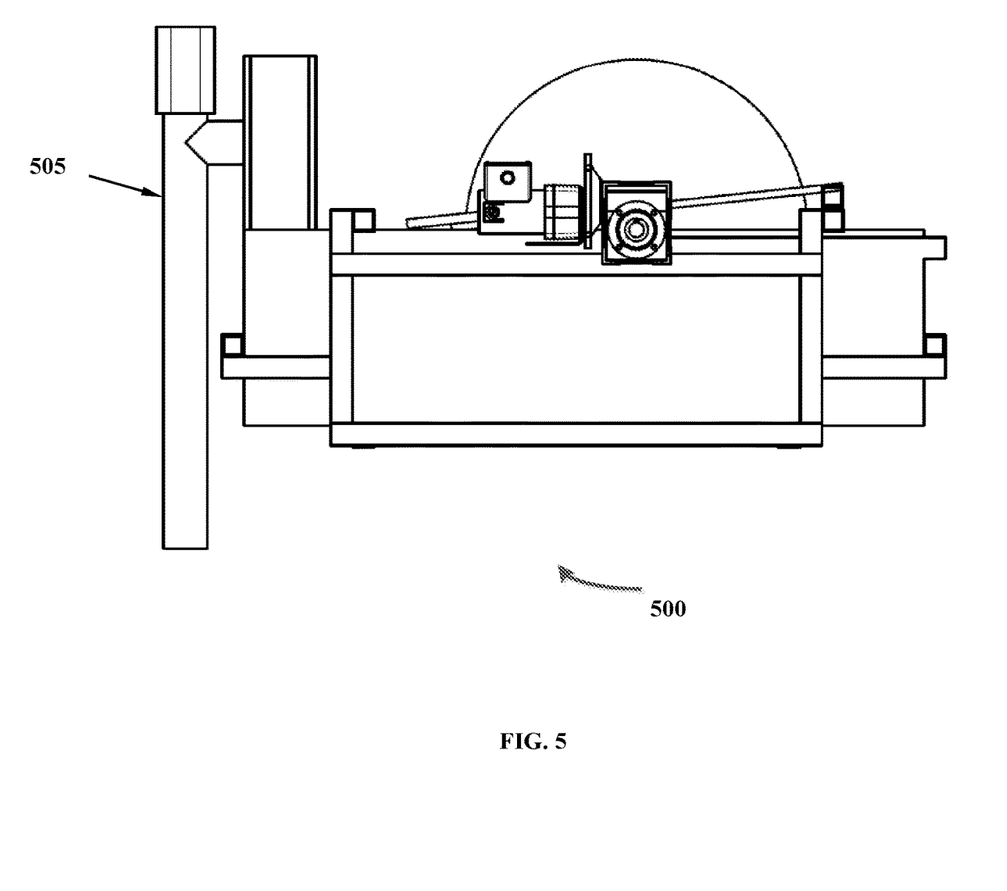

FIG. 5 depicts a side perspective of an algal harvester 500. The algal harvester 500 can be an example of algal harvester 115 or algal harvester 400 with reference to FIGS. 1 and 4, respectively. FIG. 5 provides another view of the pump 505, which can be an example of pump or pump 405, with reference to FIGS. 1 and 4, respectively.

Figure 6:
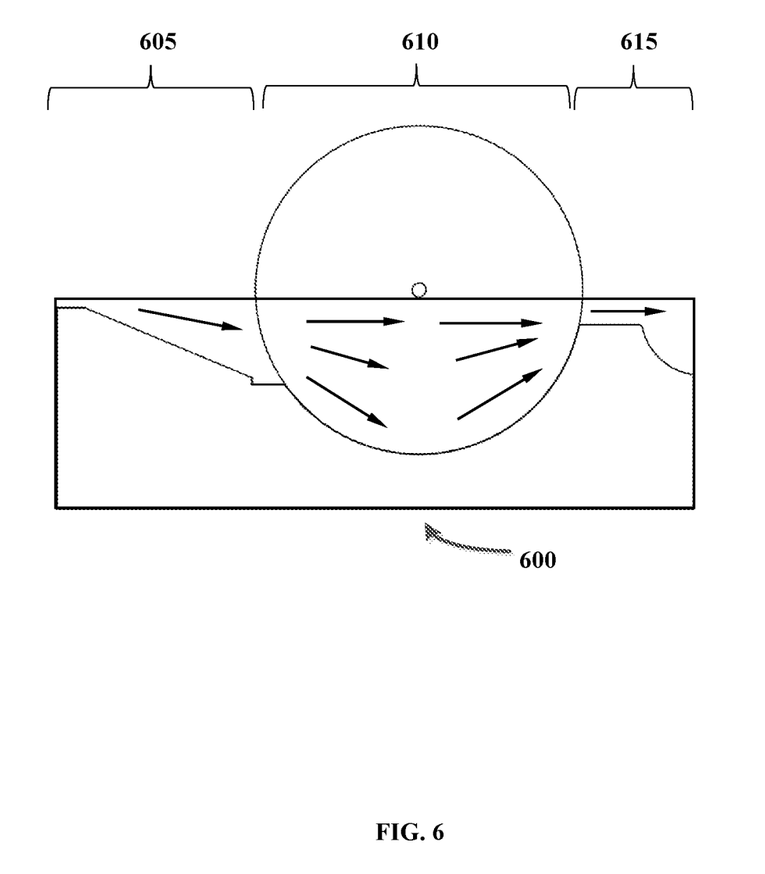
FIG. 6 depicts a flow profile for a magnetic algae harvester, in accordance with embodiments of the claimed invention.

FIG. 6 depicts a flow profile 600 for algae through a harvester, according to embodiments of the claimed invention. In some examples, the flow profile 600 depicts a side profile of a magnetic separator, such as separator 420 as discussed with reference to FIG. 4.

The arrows shown in the flow profile 600 illustrate the direction of fluid flow throng harvester. Flow profile 600 includes a first section 605, a second section 610, and a third section 615. The first section 605 is an introduction section for the harvester. The first section 605 expands the fluid streamlines so they are evenly introduced into the separator.

The second section 610 is a separation area where the separator is located. In the second section 610, magnetic particle/algae conjugates are collected by the magnetic separator. The magnetic particle/algae conjugates can be examples of magnetic particle/algae conjugates discussed in more detail with reference to FIGS. 1-5.

The third section 615 includes an outflow area. The third section 615 regulates the material depth that the sections 605-615 experience. The flow exits the machine at port 430 as shown in FIG. 4. In some embodiments, the width of the flow profile can vary between 0.0625"-3", depending on the composition and design of the separators, as well as the desired flow rate. In some cases, higher flow rates can require wider flow profile widths.

Figure 7:
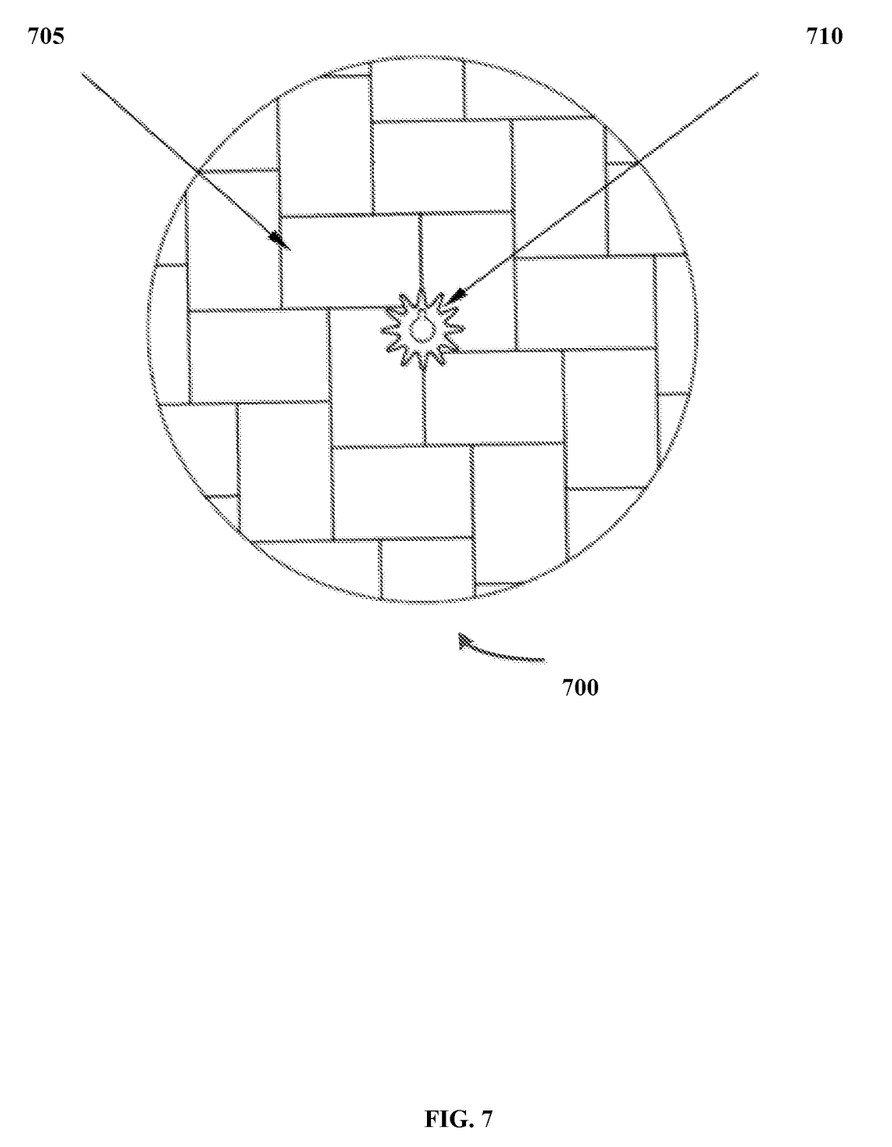
FIGS. 7 and 8 depict magnetic assemblies for a magnetic algae harvester, in accordance with embodiments of the claimed invention.

FIG. 7 depicts a magnetic disc 700 in accordance with embodiments of the claimed invention. Magnetic disc 700 can be an example of a separator 420 as described with reference to FIG. 4, and can be a component of a harvester, such as harvesters 130 and 400 as described with reference to FIGS. 1 and 4, respectively.

Magnetic disc 700 includes multiple magnetic tiles, such as magnetic tiles 705. Each magnetic tile 705 is a dipole magnet, and each magnetic tile 705 includes a north pole and a south pole. The magnetic tiles 705 can be configured in various way so as to organize the multiple north/south poles into separate designs as discussed above with reference to FIG. 4 (e.g., Halbach arrays, single north/south pole configuration, etc.).

The center of magnetic disc 700 includes a strain relief component 710. The strain relief component 710 mitigates straining on the magnetic tiles 705, which mitigates the possibility of material failure (e.g., breaking, cracking, etc.) The strain relief component 710 can be composed of plastic, but may alternatively be composed of other material suitable for relieving strain on the magnetic disc 700.

The strain relief component 710 interfaces with a drive shaft, such as drive shaft 440 as discussed with reference to FIG. 4. In some cases, the drive shaft is a keyed stainless steel drive shaft. The magnetic disc 700 is rotated about its center via the drive shaft. The magnetic disc 700 is rotated past a scraper, such as scraper 435 as discussed with further reference to FIG. 4.

Figure 8:
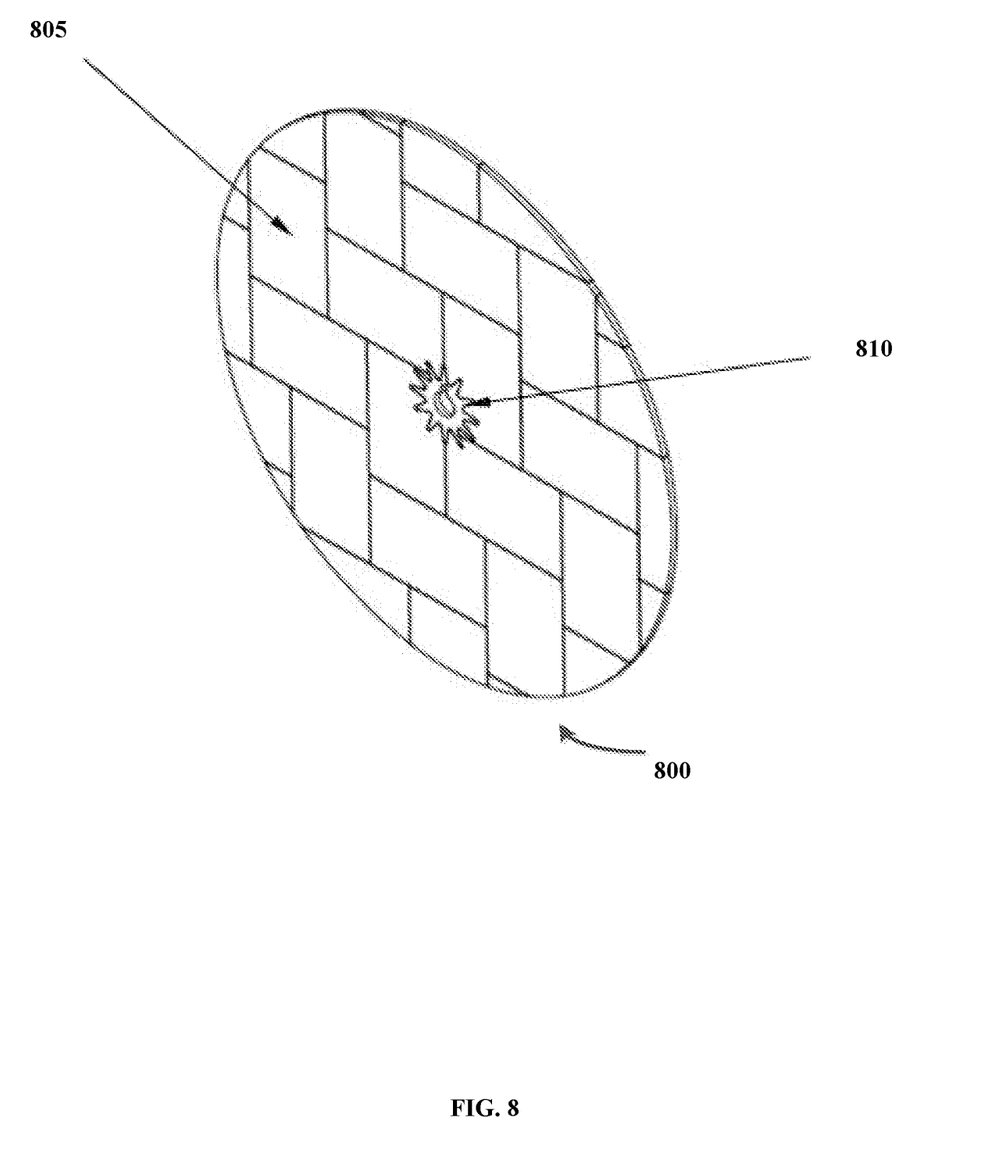

FIG. 8 depicts a magnetic disc 800 in accordance with embodiments of the claimed invention. Magnetic disc 800 can be an example of magnetic disc 700 as described with reference to FIG. 7. Magnetic disc 800 can be an example of a separator 420 as described with reference to FIG. 4, and can be a component of a harvester, such as harvesters 130 and 400 as described with reference to FIGS. 1 and 4, respectively.

Magnetic disc is in some cases be a different view of magnetic disc 700 of FIG. 7. The magnetic disc 800 includes magnetic tiles 805, which can be examples of magnetic tiles 705 of FIG. 7, and also includes a strain relief component 810, which can be an example of strain relief.

Figure 9:
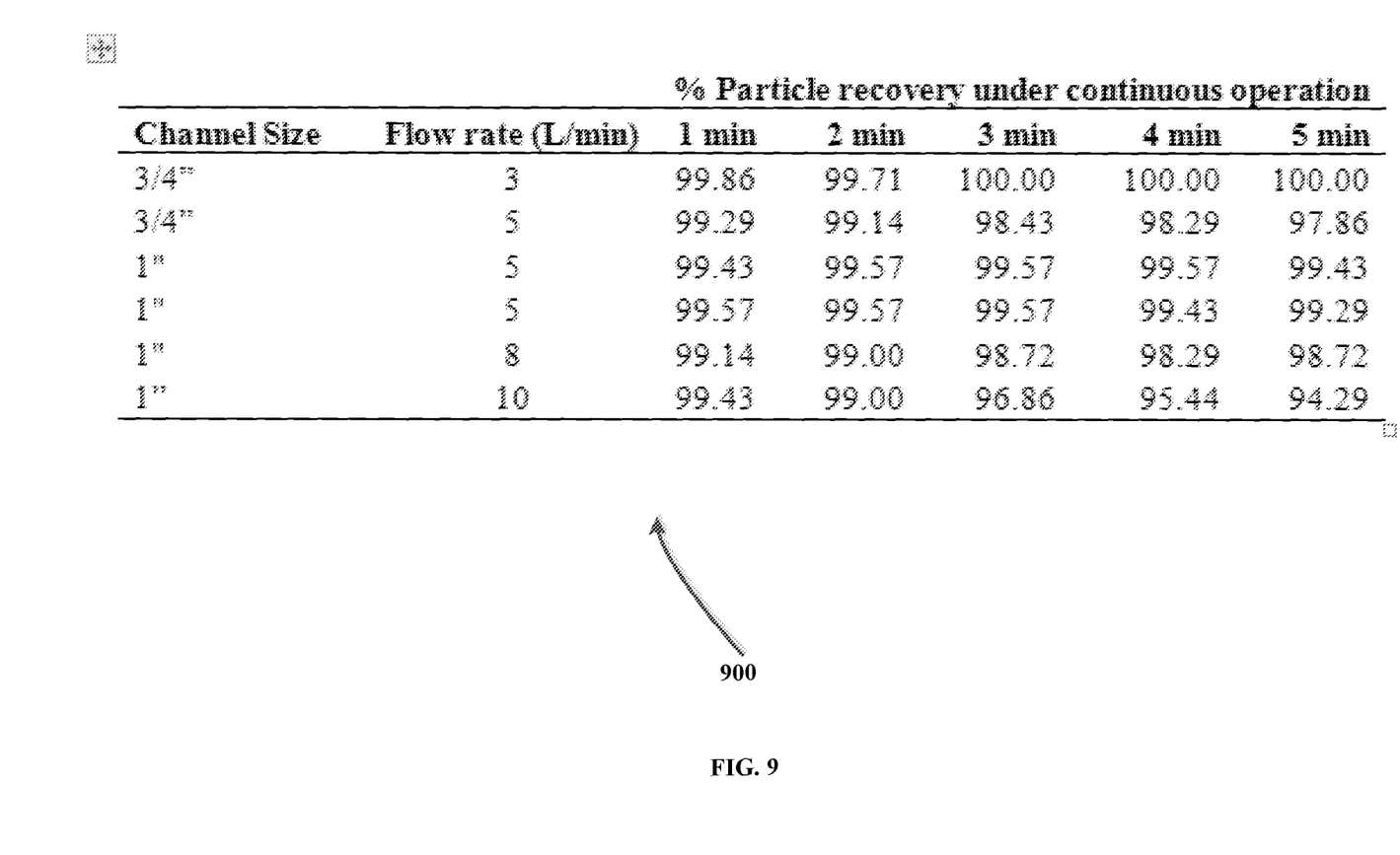
FIG. 9 depicts a magnetic particle recovery results table, in accordance with embodiments of the claimed invention.

FIG. 9 depicts particle recovery results table 900 in accordance with embodiments of the claimed invention.

The results table 900 provide testing data from a harvester taken every minute for a 5 minute span. The data show separation rates at different channel widths and at different flow rates. Both algal monocultures and multi-species polycultures have been harvested using this technology.

Figure 10:
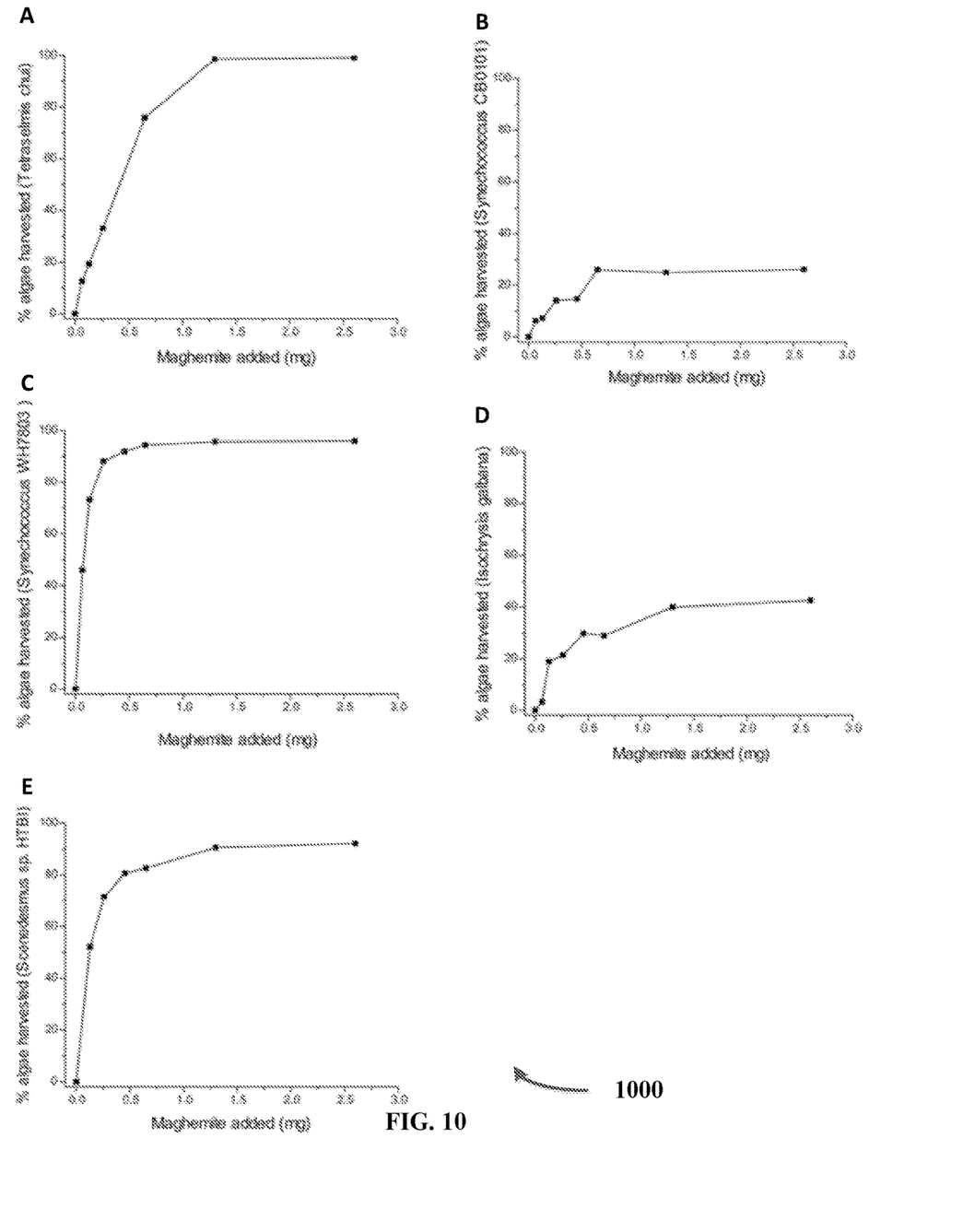
FIG. 10 depicts algal particle recovery results graphs, in accordance with embodiments of the claimed invention.

FIG. 10 depicts algal particle recovery results graphs 1000 in accordance with embodiments of the claimed invention.

Figure 11:
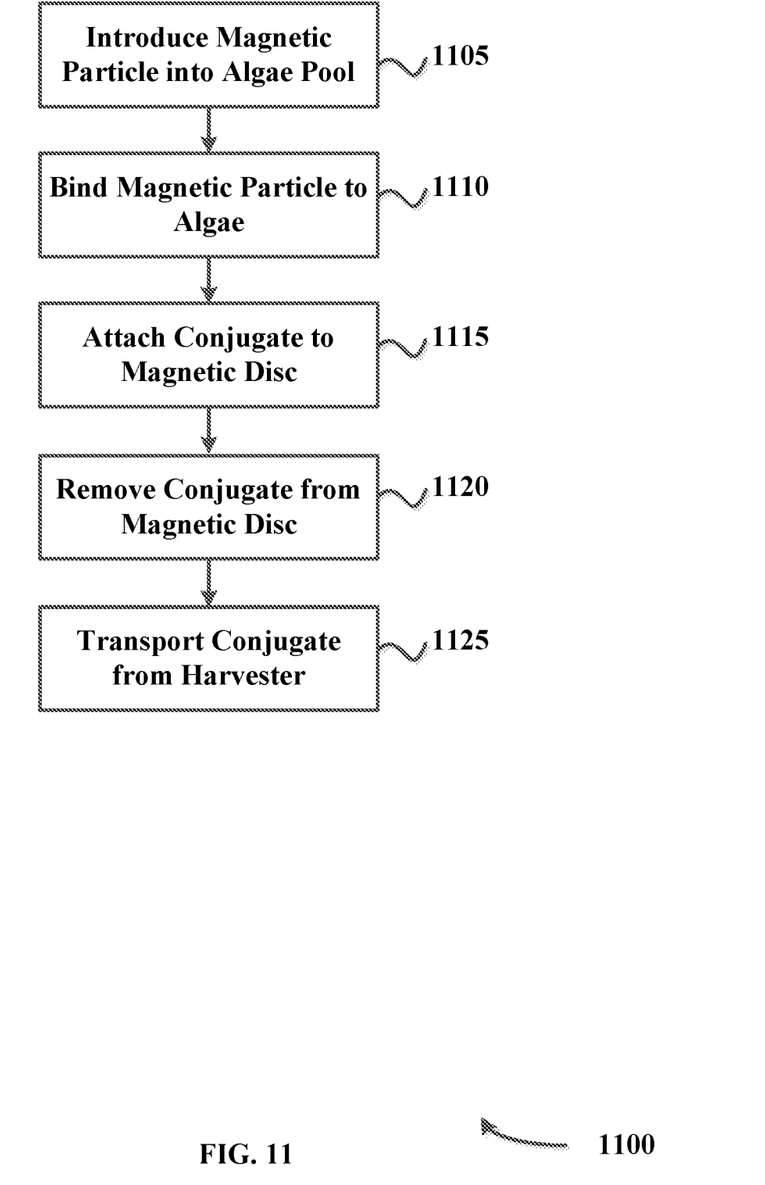
FIG. 11 depicts a workflow process for collecting and harvesting algae for biofuel conversion, in accordance with embodiments of the claimed invention.

FIG. 11 depicts a process workflow 1100 for harvesting bio fuel in accordance with embodiments of the claimed invention. The process workflow can be implemented by a harvesting system, such as system 100 as described with reference to FIG. 1.

At Step 1105, a set of magnetic particles are introduced into an algae pool containing at least one algae organism. In some cases, Step 1105 is performed by a harvester, such as harvesters 115 or 400, which are described in detail with reference to FIGS. 1 and 4, respectively.

At Step 1110, at least one magnetic particle is bound to the at least one algae organism to form at least one algae conjugate. In some cases, Step 1110 is performed by a harvester, such as harvesters 115 or 400, which are described in detail with reference to FIGS. 1 and 4, respectively.

At Step 1115, the at least one algae conjugate is attached to a surface of at least one magnetic disc of an algae harvester, when the at least one algae conjugate comes in contact with the at least one magnetic disc. Additionally or alternatively, Step 1115 is performed by a harvester, such as harvesters 115 or 400, which are described in detail with reference to FIGS. 1 and 4, respectively.

At Step 1120, the at least one algae conjugate is removed, via a scraper, from the surface of the at least one magnetic disc. In some cases, Step 1120 is performed by a harvester, such as harvesters 115 or 400, which are described in detail with reference to FIGS. 1 and 4, respectively.

At Step 1125, the at least one algae conjugate is transported from the algae harvester. In some cases, Step 1125 performed by a harvester, such as harvesters 115 or 400, which are described in detail with reference to FIGS. 1 and 4, respectively.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

What is claimed is:

1. A system for harvesting algae, the system comprising: an algae pool containing at least one algae organism; a magnetic particle storage unit configured to introduce at least one magnetic particle into the algae pool, wherein the at least one magnetic particle binds to the at least one algae organism to form at least one algae conjugate; and an algae harvester, comprising: at least one magnetic disc configured to attach, via a surface of the at least one magnetic disc, to the at least one algae conjugate when the at least one algae conjugate comes in contact with the at least one magnetic disc; and at least one scraper configured to: remove the at least one algae conjugate from the surface of the at least one magnetic disc; and transport the at least one algae conjugate from the algae harvester; wherein each of the at least one magnetic disc further comprises a strain relief component, wherein said strain relief component interfaces with a drive shaft that rotates the at least one magnetic disc; wherein the at least one magnetic disc further comprises a plurality of magnetic tiles, and wherein said strain relief component mitigates straining on the plurality of magnetic tiles; wherein aid magnetic tiles are flexibly attached; wherein each magnetic tile includes a north magnetic pole and a south magnetic pole, or wherein said plurality of magnetic tiles further comprise a plurality of north magnetic poles and a plurality of south magnetic poles, or wherein said plurality of magnetic tiles further comprise at least one Holbach array, or a combination thereof, wherein the plurality of magnetic tiles form a plurality of magnetic field lines, wherein the plurality of magnetic field lines are configured in a parallel line pattern or a grid pattern, wherein a spacing between each south magnetic pole or north magnetic pole, and an adjacent magnetic pole is between 0.06 inches and 4 inches.

2. The system of claim 1, further comprising: a conjugate separator configured to: receive the at least one algae conjugate from the algae harvester; and separate the at least one algae conjugate into the at least one magnetic particle and the at least one algae organism.

3. The system of claim 2, wherein separating the at least one algae conjugate further comprises:
reducing a calcium concentration of a solution containing the at least one algae conjugate.

4. The system of claim 2, wherein the conjugate separator further comprises a hydrodynamic shear, wherein separating the at least one algae conjugate further comprises:
shearing, via the hydrodynamic shear, the at least one algae conjugate.

5. The system of claim 2, wherein separating the at least one algae conjugate further comprises:
magnetically separating the at least one algae conjugate.

6. The system of claim 2, wherein the at least one magnetic particle is transported back to the algae pool after being separated from the at least one algae organism.

7. The system of claim 1, wherein the at least one magnetic disc is further configured to rotate along a center axis of the at least one magnetic disc.

8. The system of claim 7, wherein the scraper is further configured to remove the at least one algae conjugate from the surface of the at least one magnetic disc as the at least one magnetic disc rotates along the center axis.

9. The system of claim 1, wherein transporting the at least one algae conjugate further comprises transporting the at least one algae conjugate back to the algae pool.

10. The system of claim 1, wherein the at least one magnetic disc further comprises a plurality of magnetic tiles, wherein each magnetic tile includes:
a north magnetic pole and a south magnetic pole, or
a plurality of north magnetic poles and a plurality of south magnetic poles, or
at least one Holbach array, or
a combination thereof.

11. The system of claim 10, wherein the plurality of magnetic tiles are configured to form an aggregate north pole and an aggregate south pole for the at least one magnetic disc.

12. The system of claim 10, wherein the plurality of magnetic tiles are configured to form a closed magnetic circuit within the at least one magnetic disc.

13. The system of claim 10, wherein the plurality of magnetic tiles form a plurality of magnetic field lines, wherein the plurality of magnetic field lines are configured in a parallel line pattern or a grid pattern, wherein a spacing between each south magnetic pole or north magnetic pole, and an adjacent magnetic pole is between 0.06 inches and 4 inches.

14. The system of claim 1, wherein the algae harvester is located within or on a surface of the algae pool.

15. The system of claim 1, further comprising: an axial flow pump configured to transport the at least one algae organism from the algae pool to the algae harvester.

16. A method for harvesting algae, the method comprising: introducing at least one magnetic particle into an algae pool containing at least one algae organism; binding the at least one magnetic particle to the at least one algae organism to form at least one algae conjugate; attaching, via a surface of at least one magnetic disc of an algae harvester, to the at least one algae conjugate when the at least one algae conjugate comes in contact with the at least one magnetic disc; removing, via a scraper, the at least one algae conjugate from the surface of the at least one magnetic disc; and transporting the at least one algae conjugate from the algae harvester, wherein each of the at least one magnetic disc further comprises a strain relief component, wherein said strain relief component interfaces with a drive shaft that rotates the at least one magnetic disc; wherein the at least one magnetic disc further comprises a plurality of magnetic tiles, and wherein said strain relief component mitigates straining on the plurality of magnetic tiles; wherein each magnetic tile includes a north magnetic pole and a south magnetic pole, or wherein said plurality of magnetic tiles further comprise a plurality of north magnetic poles and a plurality of south magnetic poles, or wherein said plurality of magnetic tiles further comprise at least one Holbach array, or a combination thereof, wherein the plurality of magnetic tiles form a plurality of magnetic field lines, wherein the plurality of magnetic field lines are configured in a parallel line pattern or a grid pattern, wherein a spacing between each south magnetic pole or north magnetic pole, and an adjacent magnetic pole is between 0.06 inches and 4 inches.

17. The method of claim 16, further comprising:
receiving, by a conjugate separator, the at least one algae conjugate from the algae harvester; and
separating the at least one algae conjugate into the at least one magnetic particle and the at least one algae organism.

18. The method of claim 17, wherein separating the at least one algae conjugate further comprises:
reducing a calcium concentration of a solution containing the at least one algae conjugate.

19. The method of claim 17, wherein separating the at least one algae conjugate further comprises:
shearing, via a hydrodynamic shear, the at least one algae conjugate.

20. The method of claim 17, wherein separating the at least algae conjugate further comprises:
magnetically separating the at least one algae conjugate.

21. The method of claim 17, wherein the at least one magnetic particle is transported back to the algae pool after being separated from the at least one algae organism.

22. The method of claim 16, further comprising:
rotating the at least one magnetic disc along a center axis of the at least one magnetic disc.

23. The method of claim 22, further comprising:
removing, via the scraper, the at least one algae conjugate from the surface of the at least one magnetic disc as the at least one magnetic disc rotates along the center axis.

24. The method of claim 16, wherein transporting the at least one algae conjugate further comprises transporting the at least one algae conjugate back to the algae pool.

25. The method of claim 16, wherein the plurality of magnetic tiles are configured to form an aggregate north pole and an aggregate south pole for the at least one magnetic disc.

26. The method of claim 16, wherein the plurality of magnetic tiles are configured to form a closed magnetic circuit within the at least one magnetic disc.

27. The method of claim 16, wherein the algae harvester is located within or on a surface of the algae pool.

28. The method of claim 16, further comprising:
transporting, via an axial flow pump, the at least one algae organism from the algae pool to the algae harvester.

29. The method of claim 16, wherein said plurality of magnetic tiles are flexible attached to one another forming said magnetic disc.

* * * * *

UNITED STATES PATENT AND TRADEMARK OFFICE
CERTIFICATE OF CORRECTION

| | | |
|---|---|---|
| PATENT NO. | : 11,904,326 B2 | Page 1 of 1 |
| APPLICATION NO. | : 17/048385 | |
| DATED | : February 20, 2024 | |
| INVENTOR(S) | : Ryan Joseph Powell et al. | |

It is certified that error appears in the above-identified patent and that said Letters Patent is hereby corrected as shown below:

In the Specification

In Column 1, Line 13 please insert after the heading CROSS REFERENCE TO RELATED APPLICATIONS:
-- STATEMENT REGARDING FEDERALLY SPONSORED RESEARCH
This Invention was made with U.S. Government support under Contract No. DE-SC00013837 awarded by the Department of Energy. The Government has certain rights in this invention. --

Signed and Sealed this
Twenty-first Day of May, 2024

Katherine Kelly Vidal
*Director of the United States Patent and Trademark Office*